(12) United States Patent
Geng et al.

(10) Patent No.: US 7,208,085 B2
(45) Date of Patent: Apr. 24, 2007

(54) CAKY CHROMATOGRAPHIC COLUMN AND THE METHOD FOR PRODUCING IT AND ITS APPLICATIONS

(75) Inventors: Xindu Geng, Xi'an (CN); Yangjun Zhang, Xi'an (CN)

(73) Assignee: Northwest University, Xi'an (CN)

( * ) Notice: Subject to any disclaimer, the term of this patent is extended or adjusted under 35 U.S.C. 154(b) by 110 days.

(21) Appl. No.: 10/477,977

(22) PCT Filed: May 16, 2002

(86) PCT No.: PCT/CN02/00333

§ 371 (c)(1),
(2), (4) Date: May 24, 2004

(87) PCT Pub. No.: WO02/095390

PCT Pub. Date: Nov. 28, 2002

(65) Prior Publication Data

US 2004/0195161 A1    Oct. 7, 2004

(30) Foreign Application Priority Data

May 18, 2001   (CN)   ................................ 01 1 15263
May 18, 2001   (CN)   ................................ 01 1 15264

(51) Int. Cl.
*B01D 15/08*    (2006.01)
(52) U.S. Cl. ................ 210/198.2; 210/198.3; 210/656
(58) Field of Classification Search ............ 210/198.2, 210/656, 657, 658, 659, 198.3; 96/101, 105, 96/107

See application file for complete search history.

(56) References Cited

U.S. PATENT DOCUMENTS 3,780,866 A * 12/1973 Ek et al. ................... 210/198.2

(Continued)

FOREIGN PATENT DOCUMENTS

EP   1 074 835 A1   7/2000

(Continued)

OTHER PUBLICATIONS

Machine Translation of Japan Patent No. 7-301626.*

*Primary Examiner*—Ernest G. Therkorn
(74) *Attorney, Agent, or Firm*—David Silverstein; Andover-IP-Law

(57) ABSTRACT

The present invention discloses a new and improved kind of chromatographic cake and its manufacturing methods and applications. The objective of this invention is to provide an improved chromatographic apparatus and methods for manufacturing such an apparatus, whereby the separation and simultaneous renaturation and purification of biopolymers can be efficiently performed with excellent results. The chromatographic cakes of this invention generally comprise a chromatographic packing cake with a mobile phase inlet and a mobile phase outlet, together with a chromatographic packing packed into an inner cavity region of the chromatographic packing cake. The ratio of the thickness to the diameter of the inner cavity region of the chromatographic packing cake is less than or equal to 1. A method of manufacturing such chromatographic cakes generally comprises the steps of: 1) Manufacturing the chromatographic packing cake, wherein the chromatographic packing cake includes combined upper and lower clamp plates having, respectively, a mobile phase inlet or outlet, and a cake body with at least one lateral hole or aperture; wherein the ratio of the thickness to the diametral dimension of the inner cavity of the chromatographic packing cake is smaller than or equal to 1; and, 2) adding chromatographic packing in whole or at least in part using the lateral hole(s) of the chromatographic packing cake to fill the inner cavity of the chromatographic-packing cake with a suitable packing material.

17 Claims, 9 Drawing Sheets

U.S. PATENT DOCUMENTS

| | | | |
|---|---|---|---|
| 4,497,711 A * | 2/1985 | Shepherd | 210/656 |
| 4,557,830 A * | 12/1985 | Onitsuka et al. | 210/198.2 |
| 4,582,608 A * | 4/1986 | Ritacco | 210/656 |
| 4,710,289 A * | 12/1987 | Wermuth et al. | 210/198.2 |
| 4,722,786 A * | 2/1988 | Weaver | 210/198.2 |
| 4,732,687 A * | 3/1988 | Muller et al. | 210/656 |
| 4,737,284 A * | 4/1988 | Hauke et al. | 210/198.2 |
| 4,737,292 A * | 4/1988 | Ritacco et al. | 210/656 |
| 4,806,238 A * | 2/1989 | Sattler et al. | 210/198.2 |
| 4,865,729 A * | 9/1989 | Saxena et al. | 210/198.2 |
| 5,089,125 A * | 2/1992 | Hart et al. | 210/198.2 |
| 5,141,635 A * | 8/1992 | LePlang et al. | 210/198.2 |
| 5,238,556 A * | 8/1993 | Shirkhan | 210/198.2 |
| 5,324,426 A * | 6/1994 | Joseph et al. | 210/198.2 |
| 5,589,062 A * | 12/1996 | Rice | 210/198.2 |
| 5,667,676 A * | 9/1997 | Alaska | 210/198.2 |
| 5,693,223 A * | 12/1997 | Yamada et al. | 210/198.2 |
| 5,863,428 A * | 1/1999 | Ma et al. | 210/198.2 |
| 6,001,253 A * | 12/1999 | Conroy et al. | 210/635 |
| 6,080,616 A * | 6/2000 | Kim | 438/239 |
| 2004/0140252 A1* | 7/2004 | Gebauer | 210/198.2 |

FOREIGN PATENT DOCUMENTS

| | | | |
|---|---|---|---|
| JP | 7-301626 | * | 11/1995 |
| RU | 2 060 498 C1 | | 5/1996 |

* cited by examiner

US 7,208,085 B2

CAKY CHROMATOGRAPHIC COLUMN AND THE METHOD FOR PRODUCING IT AND ITS APPLICATIONS

REFERENCE TO RELATED APPLICATIONS

This application is a 371 of PCT/CN20/00333 filed May 16, 2002.

TECHNICAL FIELD

This invention relates to a kind of chromatographic cake and its manufacturing method and application, especially to a kind of chromatographic cake and its manufacturing method and application which is applicable to biopolymer separation or renaturation with simultaneous purification.

BACKGROUND OF THE INVENTION

Chromatography and capillary electrophoretic methods are two means used frequently for the separation of biopolymers. Because of the limitation of the quantity of the employed mobile phase in capillary electrophoretic method, however, such methods can generally only be used on an analytical scale. Chromatography is now the most important and the most effective separation method for the separation, renaturation and purification of biopolymers. It would be desirable to be able to use such technique not only for analytical scale, but also for production scale.

When chromatography is used for separation, it is commonly accepted that the separating effect is proportional to the number of column plates, e.g., column length. If the column is too long, however, it is too expensive and it leads to a higher column pressure, which must be controlled with a high performance liquid chromatograph. It is reported in the literature that evidence can be obtained showing effective biopolymer separation with a short column using the stoichiometric displacement model for solute-in-liquid chromatography; and, a packed column of 2 mm in length using a slice of membrane having a thickness of about 2 mm that is cut off from a continuous rod is used to make biopolymer separations with good results when used on an analytical scale. It is still unknown, however, whether such a short column with stable effects can be utilized for industrialized production, as well as to what degree such a column can be shortened and still be effective.

At present, a column for high performance liquid chromatography employed at a production scale level is generally packed with particles having a diameter of about 20–30 μm. It is ideal that the ratio of column length to diameter be about 10 or less to avoid a too-high column pressure under conditions of high flow rate, thereby causing decreasing separation effects. In order to ameliorate the fact that the volume of the column bed always becomes effectively smaller under the pressure accumulated by the soft matrix over an increased column length, Pharmacia Co., which is famous around the world for its production of chronographic media adapted for use at low and middle pressure conditions, has offered a cake-shaped chromatographic column with shorter thickness (but having a length of at least 10 cm) and of greater diameter. When in use, several cake-shaped chromatographic columns of this type would typically be connected together in series. Therefore, the sum of the lengths of these serially connected columns is still many times greater than the diameter of an individual cake-shaped column, so the flow rate through this series of chromatographic cakes still cannot be too high when it is applied.

Many proteins expressed with E. coli in biotechnology exist in the form of inclusion body in E. coli because of its high hydrophobicity. Although the primary structures of such proteins may be correct, their third or fourth structures are basically wrong. As the inclusion body generally has the property of high hydrophobicity, it should be dissolved with a denaturant at high concentration, such as 7.0 mol/L guanidine hydrochloride (GuHCl) or 8.0 mol/L urea. Then the renaturation of the proteins can be processed. In the current technology, the dialysis method and the dilution method are commonly used for protein renaturation. Nevertheless, these two methods not only have a low renaturation effect (on the order of about 5%–20% generally), but they also require too much time resulting in failure to realize the objective of separating impure proteins. One alternative technology has been developed in which a denatured protein is renatured and simultaneously purified by high performance hydrophobic interaction chromatography (HPHIC). However, if some precipitates of proteins occur by sample injection, the chromatographic column in this technique will be blocked or damaged. Thus, the denatured facilities currently used for protein renaturation and purification and the multifunctional protein-purifying unit as described above have major limitations which reduce their utility and effectiveness.

It can be concluded that the following major problems currently exist in the separation and purification of proteins in various biotechnology processes:

1. Separation and purification of biopolymers made in a glass column, a plastic column or a stainless steel column, packed by soft based media, and having large diameters. The shortcomings of these processes include low column efficiency, need for large volumes of media, high consumption of mobile phase, and long production periods.

2. When small solutes are separated with a chromatographic column, the resolution should be proportional to the column length. The ratio of column diameter to column length is normally about 1:10. The column length has a small effect on the resolution of biopolymers. In general, a column with a length of about 5 cm is selected. When such a column is packed with small particles, the chromatographic system through pressure is obviously increased. Such a column should therefore be used with a high-pressure liquid chromatograph, but this results in increased production costs. Such increased costs counterbalance some of the advantages of using a column packed by small particles, namely high efficiency, large volume and good reproducibility.

3. For the usual chromatographic columns, it is preferred that samples having a high viscosity not enter the columns, and that no more than a small quantity of precipitates from samples are allowed to settle in the column head. In practice, however, the inlet and outlet conditions of the mobile phase cannot readily be changed, so such control is not convenient for the operation.

4. In a usual separation and purification process, relatively pure products can be obtained only through the sequential steps of renaturation, removal of denaturants, coarse purification, and multistep fine purification. These steps represent a long and cumbersome processing technology usually involving great loss of mass and bioactivity and, thus, with a relatively low recovery (generally no higher than about 5–20%).

5. Common renaturation methods include a dilution method and a dialysis method. With the dilution method, many dilution steps should be taken to gradually decrease the concentration of the denaturing agent employed. Thus, such a process brings many handling difficulties for the later separation and purification steps if, at each stage, samples are diluted tens, or even hundreds, of times. The dialysis method, on the other hand, takes too much time (e.g., 24 hours for only one dialysis step generally), and, furthermore, the dialysis agent should be changed many times. In addition, with the above two renaturation methods, the subject proteins are easily aggregated and precipitated resulting in a long renaturation time during the renaturation process.

6. There are many steps involved in the current separation and purification methods. In the course of such separation and processing steps, the volume of solution containing the subject proteins is always increasing. Also, each step of these methods requires substantial associated processing equipment. Therefore, current separation and purification techniques require a relatively large investment in equipment with correspondingly high production costs.

At present, for packing and manufacturing a chromatographic column, satisfactory column efficiency can be obtained when chromatographic packing material is packed using familiar axial and radial pressurization techniques. But these two methods are only applicable to the packing process for a relatively long chromatographic column wherein the ratio R of column length to diameter is greater than unity (i.e., R>1). There are no ideal packing and manufacturing methods currently available, however, for the process of packing a chromatographic "cake" wherein the ratio R of cake thickness to cake diameter is smaller than or equal to unity (i.e., $R \leq 1$). If the traditional technology were used to pack a chromatographic cake wherein $R \leq 1$, the following problems would likely occur:

1. In the traditional process to pack a chromatographic column, liquid goes through the column inlet and column outlet in the axial direction (i.e., along the axis of the column). In general, the traditional packing processes are only applicable to a chromatographic column wherein the ratio R of column length to column diameter is greater than unity.

2. Because the technique of packing columns properly requires a high level of skill, if an operator is lacking the necessary skills, circumstances may occur in which a column is not packed properly, for example having a tight outlet and/or a loose inlet. An improperly packed column has low reproducibility of results because of the defect in the column packing.

3. In a conventional chromatographic column packing process, the inlet end of the column can be made even and smooth with a blade after the column has been packed. For a chromatographic cake, however, there are no easy and effective methods to make such a large surface area of the packing, such as the inlet end of the column, even and smooth after packing the cake.

4. In general, a chromatographic column needs to be repacked after long use at high pressure. Before a column is repacked, the sunken inlet end of a chromatographic column is typically repaired to prolong column life. In order for the sunken inlet end of a chromatographic column to be repaired, however, the column head must be dismantled to remove the frit. For a column with a relatively small diameter, it is generally easy to remove the frit because of the small surface area of the frit. But, the surface area of the inlet end of a "chromatographic cake" is generally more than one up to 100 times or more greater than that of a comparable conventional chromatographic column. Also because the distributor is tabled tightly with the frit, and is normally also relatively tightly pressed in the groove of the column body, it is difficult to remove it. If it is removed with force, the distributor could often be damaged.

5. When packing having a small diameter is to be packed into a chromatographic cake using the high pressure slurry method, possible leakage must be tested before the cake can be packed because the diameter of a chromatographic cake is relatively great and, accordingly, it is difficult to seal it off if there is a leak. After the chromatographic packing is packed, if there is still a leakage problem, it can create great difficulties for repairing the apparatus.

6. For a relatively large chromatographic cake, a relatively large slurry tank and associated devices are required which increase the production costs.

SUMMARY OF THE INVENTION

The principal object of this invention is to provide a kind of improved chromatographic cake applicable to the separation, or renaturation with simultaneous purification, of biopolymers with good results.

The present invention is directed to a type of chromatographic "cake," which comprises a chromatographic packing cake or shell defining a fixed volume inner region or cavity, and having a mobile phase inlet and a mobile phase outlet, the chromatographic packing cake being packed in the inner cavity thereof with a suitable chromatographic packing material, wherein the ratio R of the thickness In a preferred embodiment of this invention, the preferable dimensions of the fixed volume inner cavity of the chromatographic packing cake range from about 0.2–50 mm in thickness and from about 5.0–1000 mm in diameter.

A chromatographic packing cake in accordance with a preferred embodiment of this invention includes upper and lower clamp plates sandwiching a cake body element, each clamp plate having either the said mobile phase inlet or outlet respectively at opposite ends (clamp plates) of the apparatus, and also, preferably, wherein the cake body includes at least one lateral hole or aperture.

In order to avoid the loss of chromatographic packing from the inner cavity, frits are assembled or located at the lateral sides of the upper and lower clamp plates respectively of the chromatographic packing cake and near to the inner cavity of the chromatographic packing cake. The diameters of the frit holes in the frits should be greater than the typical size of the biopolymers in the mobile phase but also less than the size of the chromatographic packing.

In order to obtain generally even distributions of mobile phase and solute through the cake, and to enhance the separation effect, in another preferred embodiment of the invention distributor elements are assembled or located between the upper and lower clamp plates of the chromatographic packing cake.

Such a distributor element comprises one generally flat plate having substantially the same profile as the cross section of the inner cavity of the chromatographic packing cake. On the surface of at least one lateral side of each distributor element are radiating and concentric circular blast grooves. Distributing holes are located at the junctions of the radiating and circular guide grooves.

The preferred cross section of the guide grooves in the distributor elements is generally triangular and cambered.

The diameters of the distributing holes in the distributor elements may increase gradually as they move radially outward from the center of the distributor element.

In another embodiment of chromatographic packing cakes in accordance with this invention, a seal ring may be placed between the upper and lower clamp plates and the cake body.

Chromatographic cakes in accordance with this invention may be advantageously used in the separation and purification of biopolymers prepared in biotechnology processes, thereby realizing advantages such as high efficiency, processing of large volumes and good reproducibility of results. The packed chromatographic cakes of this invention are equally useful under process conditions of either low or middle pressures. The cakes of this invention can decrease costs and enhance output. With the chromatographic cakes of this invention, the processes of separation and purification, removal of denaturants during a renaturation process, coarse purification, and multiple-step purifications can be combined and accomplished in only one step. The chromatographic cakes of this invention can work under pressure conditions ranging from about 1–200 kg/cm$^2$.

A second objective of this invention is to provide new and improved manufacturing methods for preparing chromatographic cakes in accordance with this invention, such methods being characterized by high speed, low cost and high efficiency.

In order achieve this objective, this invention uses the following technical outline of a manufacturing method for chromatographic cakes, the method including the following steps:

1. Manufacturing the chromatographic packing cake: The chromatographic packing cake includes the upper and lower clamp plates, having respectively either a mobile phase inlet or outlet, assembled together to the cake body, which has at least one lateral hole. The ratio of the thickness to the diameter of the inner cavity of the chromatographic packing cake is smaller than or equal to 1.
2. A suitable chromatographic packing is packed into the assembled cake using the lateral hole(s) of the chromatographic packing cake to insert the packing material into the inner cavity of the chromatographic packing cake.

The lateral hole(s) of the chromatographic packing cake can be directly connected to the slurry tank of a high-pressure slurry packing machine for packing the chromatographic cake.

When a chromatographic cake with a diameter of less than about 50 mm is manufactured, the chromatographic cake can be directly placed on the high-pressure slurry packing machine. According to the usual method for packing a column, the chromatographic packing can be directly added into the inner cavity of the chromatographic packing cake.

When a chromatographic cake having a diameter greater than about 50 mm is manufactured, however, the cake should preferably be at least partially packed using a suction method in order to insure that the chromatographic packing are packed tightly. Using the suction method, the chromatographic cake is placed on the high-pressure slurry-packing machine, and the chromatographic packing is added through the lateral hole(s) of the chromatographic packing cake into the inner cavity of the chromatographic packing cake.

The method of adding the chromatographic packing through the lateral hole of the chromatographic packing cake helps to reduce or eliminate the "dead" volume in the chromatographic cake, which in turn improves the separation effect. Dead volume tends to increase by the loss of chromatographic packing after the chromatographic packing has been in use for some time. The method of adding additional chromatographic packing is similar to the original cake packing method.

In order to eliminate accumulated impurities on the distributor elements, the frits, and the biopolymers that do not enter the packed chromatographic cake, the chromatographic cake should be periodically washed through the lateral hole of the chromatographic packing cake. Because these accumulations can increase the pressure on the chromatographic system, they can result in contaminating follow-up separated samples. A preferred washing method for the chromatographic cakes of this invention is to let buffer solution or water enter the lateral hole, which acts as an inlet, and go out from the inlet and outlet respectively in the upper and lower clamp plates.

Another embodiment of this invention is to periodically replace deteriorated chromatographic packing through the lateral hole of the chromatographic packing cake and to remove deteriorated chromatographic packing which has a low column efficiency and which makes the chromatographic system pressure increase. The removed packing is then replaced with new packing. One such method is as follows: let the upper and lower clamp plates act as inlets and use the lateral hole as the outlet; purge the deteriorated chromatographic packing with water, and repack the new chromatographic packing into the hollow interior of the cake.

The operations for the cake packing and packing replacement in accordance with this invention are very simple and easy, and they can save time and workload. As the clamp plates on both ends of the chromatographic cake would not be opened after a leakage check, and the cake can be packed directly, this design can insure a chromatographic cake free from liquid leakage and having an even surface of packing, which is favorable to enhancing the column efficiency. When a bigger chromatographic cake is packed, it does not need a larger slurry tank and other accessory equipment, which means that production costs are also reduced.

Further explanations of this invention in relation to the following figures and concrete examples appear below.

DETAILED DESCRIPTION OF THE INVENTION

EXAMPLE 1

Structure of a Chromatographic Cake in Accordance with this Invention

Figure 1:
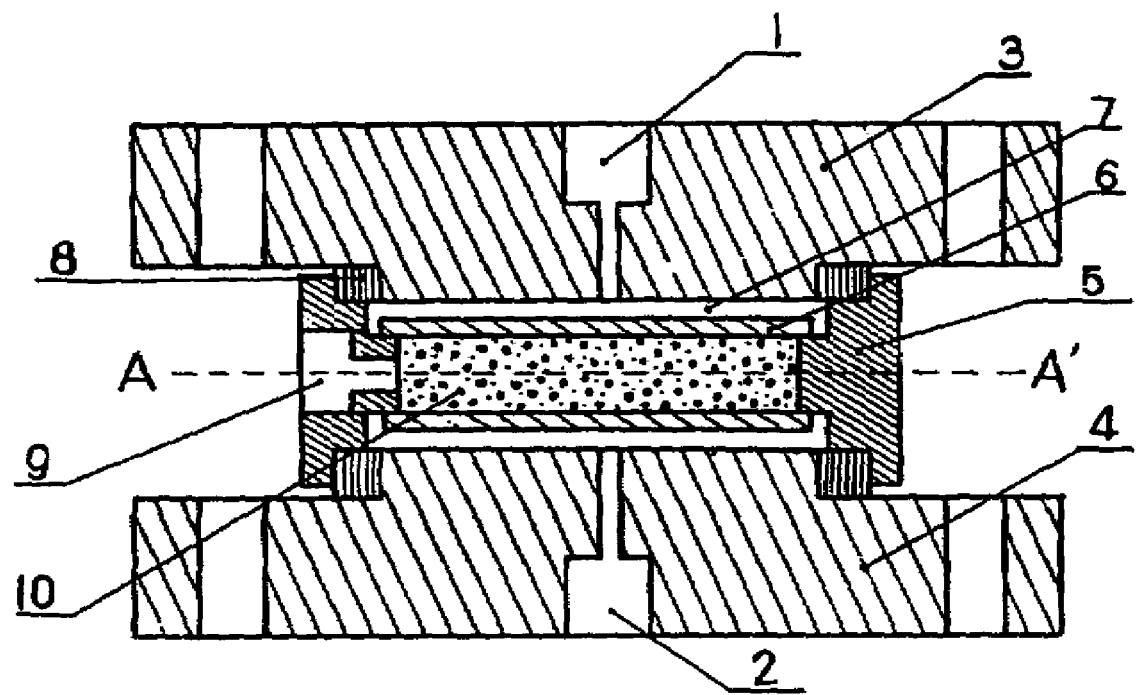
FIG. 1 is a schematic side sectional view of a chromatographic cake in accordance with this invention.
Figure 2:
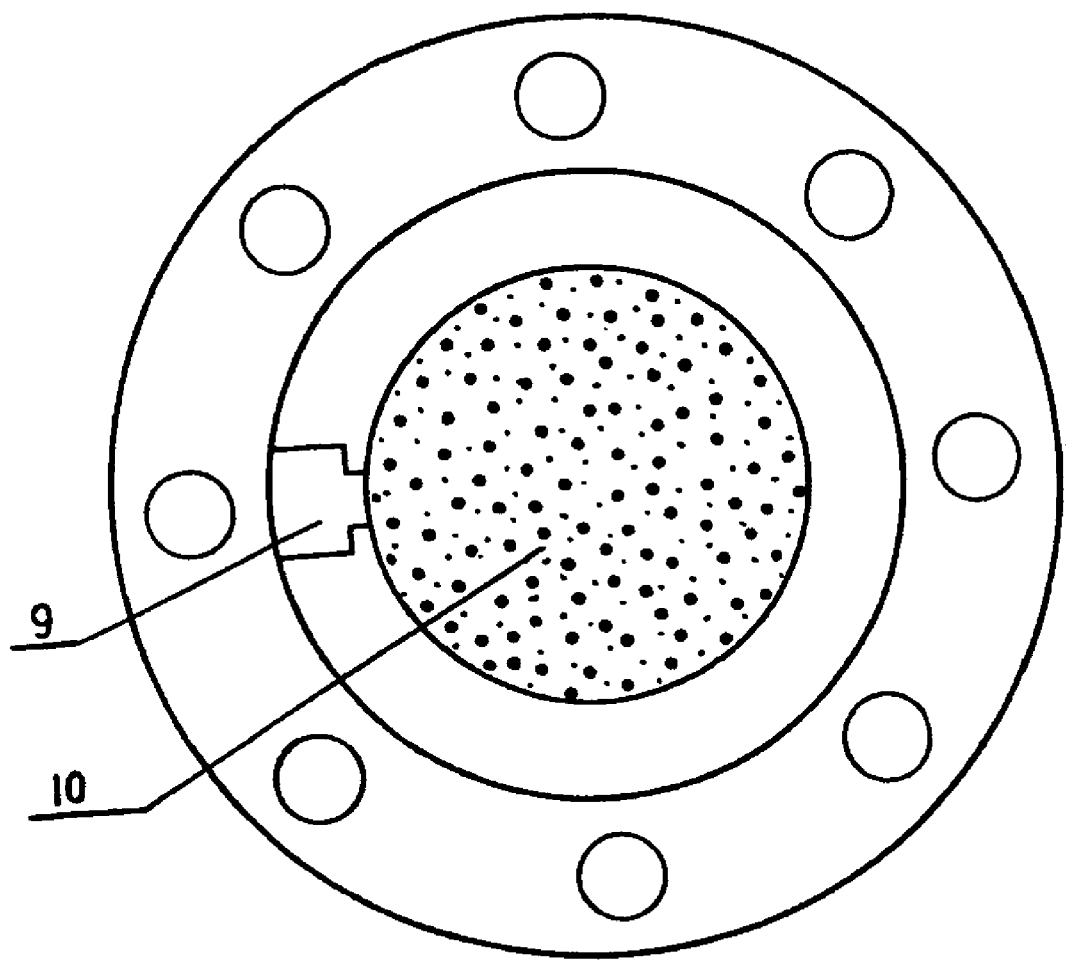
FIG. 2 is a sectional view of the chromatographic cake of FIG. 1 taken along the line A–A'.

As shown in FIGS. 1 and 2, a chromatographic cake in accordance with this invention preferably includes a stainless steel chromatographic packing cake, as seen in FIG. 1, filled with a suitable chromatographic packing 10 packed into the inner cavity of the chromatographic packing cake. The cross section of the inner cavity of the packing cake is preferably generally round in shape, with a preferred thickness of about 10 mm and having a diameter of about 100 mm. The degree of roughness on the surface of the inner cavity of the chromatographic packing cake is preferably smaller than about 1.6 μm so that it can be easily sealed and can reduce the irreversible absorption of biopolymers.

A chromatographic packing cake in accordance with this invention comprises a pair of upper and lower clamp plates, 3 and 4 respectively in FIG. 1, with a mobile phase inlet 1 in one such clamp plate and a mobile phase outlet 2 in the other such clamp plate, together with a cake body 5 having at least one lateral hole or aperture 9 extending from an external region into the inner cavity of the cake. The upper and lower clamp plates 3 and 4 and the cake body 5 define the inner cavity of the chromatographic packing cake. The lateral hole 9 through cake body 5 is designed to be blocked and sealed with an end cap (not shown) after the chromatographic packing 10 has been packed into the inner cavity. In order to prevent leakage, the seal rings 8, preferably made of corrosion-resistant engineering plastic, are installed between the upper and lower clamp plates 3 and 4 respectively and cake body 5. Stainless steel frit elements 6 with holes (not seen in FIG. 1 because they are too small) are installed separately on the inner sides of the upper and lower clamp plates 3 and 4 adjacent the inner cavity of the chromatographic packing cake. The diameter of the frit 6 is greater than the diameter of the inner cavity of the chromatographic packing cake. The diameter of the frit holes is selected to be a size that is smaller than the diameter of the particles of chromatographic packing 10 but larger than the average size of typical biopolymers being processed.

Figure 3:
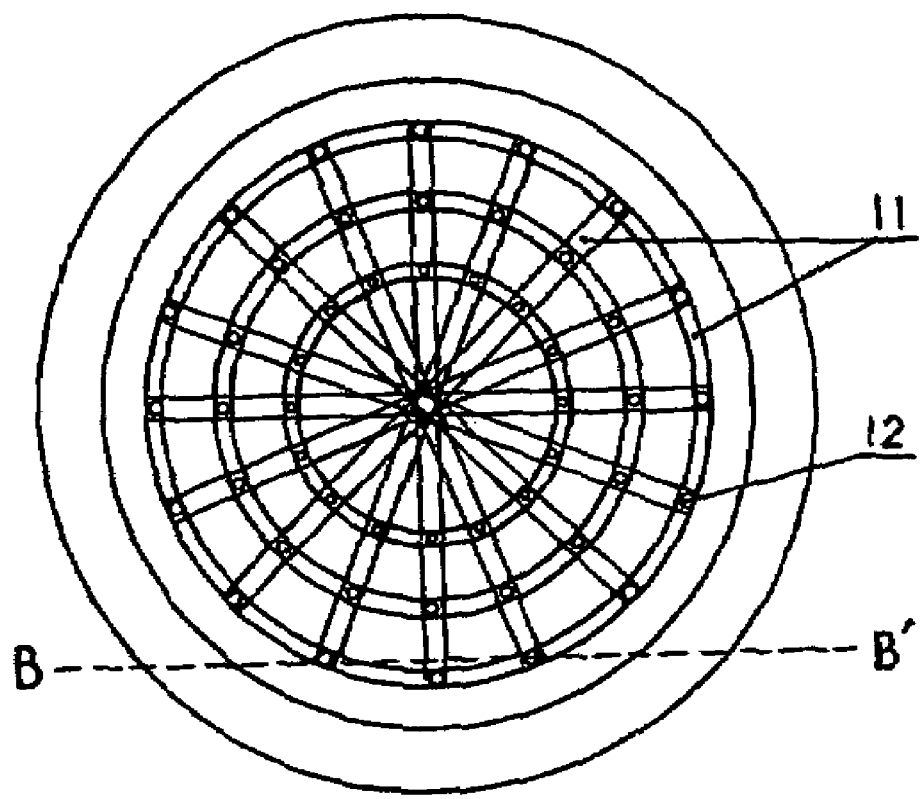
FIG. 3 is a schematic top view of a distributor element for use with a chromatographic cake in accordance with this invention.
Figure 4:
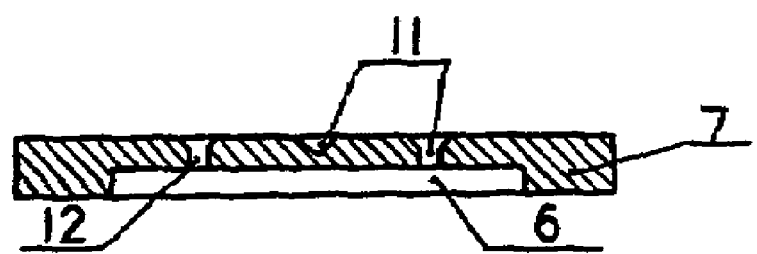
FIG. 4 is a sectional view of the distributor element of FIG. 3 taken along the line B–B'.

As shown in FIGS. 3 and 4, the distributor elements 7 used in a preferred embodiment of this invention are preferably made of engineering plastic, which is resistant to acid and alkali. Such distributor elements are installed between the upper and lower clamp plates 3 and 4, respectively, and the associated frit 6. A distributor element 7 comprises a plate member that has the same general shape as the shape of the cross section of the inner cavity of the chromatographic packing cake. On the surfaces of one or both sides of the plate are both radiating and concentric circular blast grooves 11 (same reference numeral used to identify both types of grooves). The cross section of the blast grooves 11 is preferably of a generally triangular shape. In the junctions between the radiating and circular blast grooves 11, are generally round distribution holes 12. In one embodiment of this invention, the diameters of the distribution holes may increase gradually as they are located further radially outward from the center of the distribution element. Such increasing size of the distribution element holes 12 can be seen in FIG. 3.

In practice, the cross section of the inner cavity of a chromatographic packing cake in accordance with this invention may have many different shapes, for example, it can be round, polygonal, elliptic and so on. But, in each such design, the ratio of the thickness to the diameter (or corresponding dimension) of the inner cavity of the chromatographic packing cake should be smaller than or equal to 1. An optimal cake thickness has been found to be about 0.2–50 mm, with the corresponding diametral dimension ranging from about 5.0–1000 mm. The chromatographic packing cake can be made from many materials, such as resistant-to-acid and alkali stainless steel, titanium alloy, and many kinds of engineering plastics. There are also many kinds of chromatographic packing suitable for various types of chromatographic separations which are useful with the chromatographic cakes of this invention. The number of lateral holes 9 on the cake body 5 of the chromatographic packing cake may be one or more than one, which can be decided in accordance with each actual situation.

EXAMPLE 2

Packing and Manufacturing a Medium-Larger Sized Chromatographic Cake with a Diameter of more than 50 mm Using the Radial Column Packing Method 1. A chromatographic cake was made in accordance with the method described above in Example 1 and as illustrated in FIGS. 1–4;
2. The cake was at least partially packed using a usual suction packing method; and,
3. The lateral hole(s) 9 of the chromatographic packing cake was (were) connected directly with the slurry tank on a high-pressure slurry-packing machine, and additional chromatographic packing was added through the lateral hole(s) of the chromatographic packing cake into the inner cavity of the chromatographic packing cake to complete the packing step.

EXAMPLE 3

Packing and Manufacturing a Smaller-Sized Chromatographic Cake with a Diameter of less than 50 mm Using the Radial Column Packing Method 1. A chromatographic packing cake was made according to the method described above in Example 1 and as illustrated in FIGS. 1–4; and,
2. The lateral hole(s) 9 of the chromatographic packing cake was (were) connected directly with the slurry tank on a high-pressure slurry-packing machine, and the chromatographic packing was added through the lateral hole(s) of the chromatographic packing cake into the inner cavity of the chromatographic packing cake to fill the inner cavity.

EXAMPLE 4

Performance Comparison Between Two Methods of Packing a Chromatographic Cake

Figure 5:
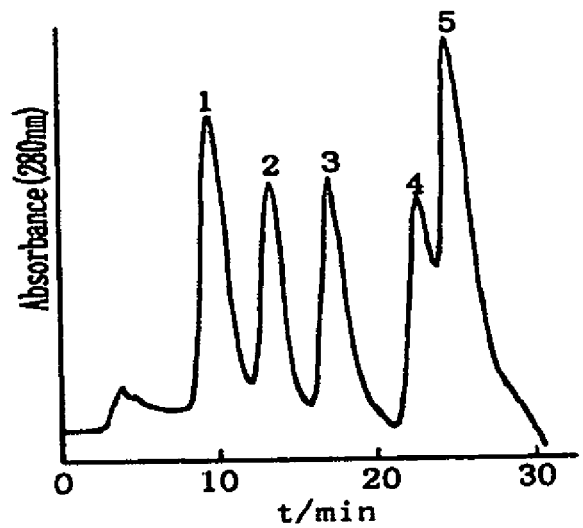
FIG. 5 is a chromatogram of a chromatographic cake in accordance with this invention which has been radially packed.
Figure 6:
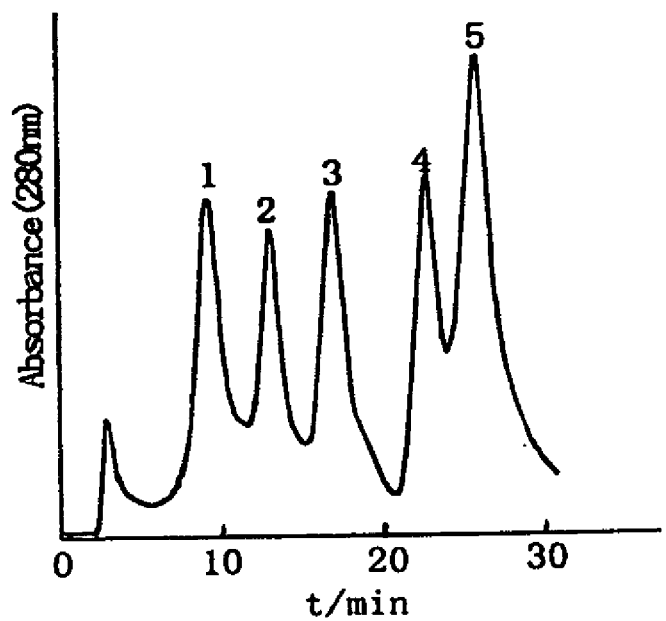
FIG. 6 is a chromatogram of a chromatographic cake in accordance with this invention which has been axially packed.

Under the same cake packing conditions (40 MPa column/cake packing pressure and 30 min. column packing time), small particles (diameter of about 5 μm of a hydrophobic chromatographic packing were packed separately into two identical 10×50 mm I.D. chromatographic cakes first using the usual axial column packing method and, second, using the radial column packing method of this invention. Under the same chromatographic conditions (flow rate of 5.0 mL/min and gradient of 0–100% B for 25 min.), five proteins (cytochrome C, ribonuclease A, lysozyme, α-amylase and insulin) were separated using the two packed cakes. The above operation was repeated five times for each cake. The chromatograms showing the results of the two packing methods are respectively shown in FIGS. 5 and 6. In the Figures, peak 1=cytochromoid C, peak 2=ribonuclease A, peak 3=lysozyme, peak 4=α-amylase and peak 5=insulin. Comparing FIGS. 5 and 6, it can be seen from the results in the Figures that good, substantially similar separation results are obtained with both of the column packing methods for the standard protein separation. One difference found with this Example was that the radial packing method had somewhat better reproducibility of results than the axial column packing method.

EXAMPLE 5

Figure 7:
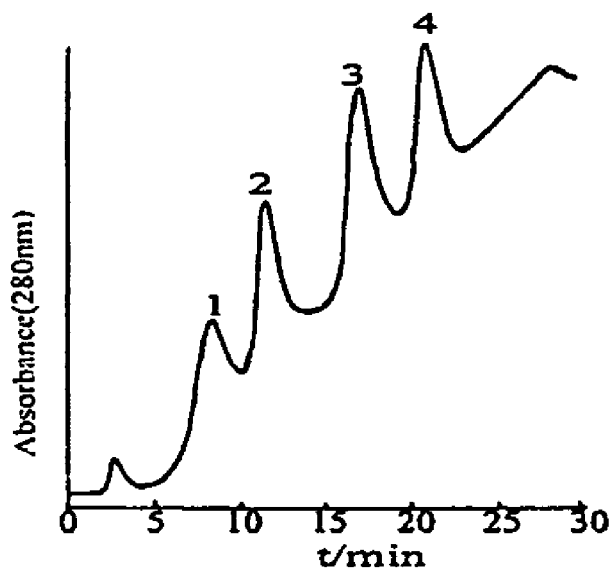
FIG. 7 is a chromatogram for a separation carried out in accordance with Example 5 below using a chromatographic cake in accordance with this invention.
Figure 8:
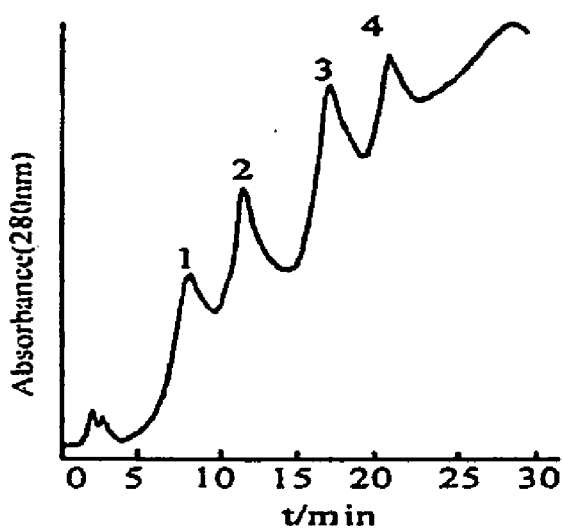
FIG. 8 is a chromatogram for a separation carried out in accordance with Example 5 below using a chromatographic cake that has been washed and repacked with additional packing in accordance with this invention.

Separation Performance After Radially Discharging and Repacking a Chromatographic Cake A hydrophobic chromatographic packing was packed through the lateral hole of a chromatographic cake using the radial high pressure slurry method, after which the lateral hole was sealed with an end cap. Under the conditions of a flow rate of 5 m L/min and a gradient of 100% A–100% B for a period of 25 mins., cytochrome C, myoglobin, lysozyme and α-amylase were separated. The results are shown in FIG. 7. In FIG. 7, peak 1=cytochrome C, peak 2=ribonuclease A, peak 3=lysozyme, and peak 4=α-amylase. Following this separation, the chromatographic cake was washed thoroughly. The lateral hole was used as a wash fluid outlet, and the inlet and outlet of the clamp plates of the chromatographic cake were used as wash fluid inlets, using water as the mobile phase. A chromatographic pump was turned on to assist with purging the used packing. Packing was added to replace deteriorated packing and any lost during the wash step. After the packing was further processed through degassing with up sonic and evenly slurried, the chromatographic cake was repacked using the same column packing method as previously. Under the same chromatographic conditions used previously, the four proteins were again successfully separated using the washed and repacked chromatographic cake. The results are shown in FIG. 8, in which peak 1=cytochrome C, peak 2=ribonuclease A, peak 3=lysozyme, and peak 4=α-amylase. From a comparison of FIGS. 7 and 8, no significant difference was seen comparing the original separation with the separation carried out after the original packing had been discharged from the lateral hole of the chromatographic cake, washed, treated and repacked in the chromatographic cake again without removal of the upper and lower clamp plates. This Example shows that it is very easy to discharge used, deteriorated packing through the lateral hole of the chromatographic cake, and then also easy to repack the cake with washed or new packing or to add additional packing.

EXAMPLE 6

Figure 9:
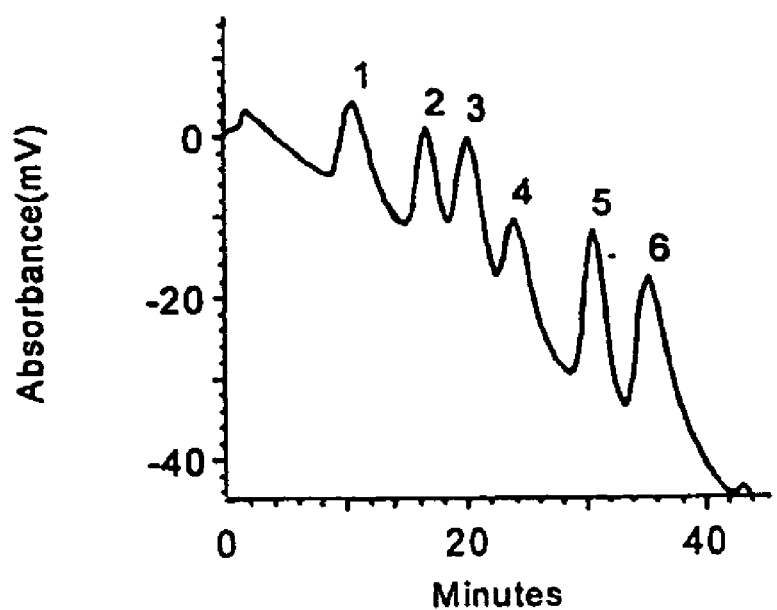
FIG. 9 is a chromatogram for a separation carried out in accordance with Example 6 below using a chromatographic cake in accordance with this invention.
Figure 10:
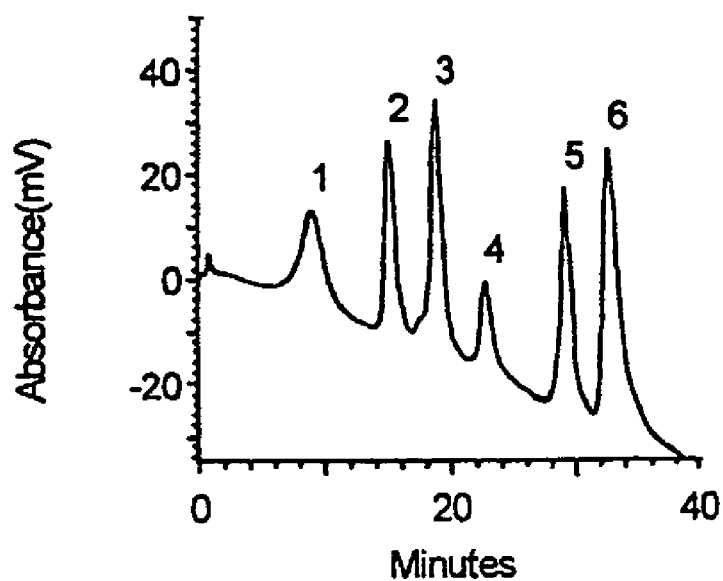
FIG. 10 is a chromatogram for a separation carried out in accordance with Example 6 but using a conventional chromatographic column instead of a chromatographic cake in accordance with this invention.

Comparison of Separations Carried out Using a Chromatographic Column and a Chromatographic Cake A chromatographic cake with the specification of 5×50 mm I.D. and a chromatographic column with the specification of 200×7.9 mm I.D. were selected for the Example. The volumes of the packing cavities in both cases was 9.9±0.2 mL. Under the same 40 MPa pressure conditions, both chromatographic apparatuses were packed using the same batch of HPHIC packing. Under the conditions of same sample size and flow rate of 4.0 ml/min., six standard proteins were separated using the two chromatographic devices. The results are shown in FIGS. 9 and 10, respectively, in which peak 1=cytochrome C, peak 2=myoglobin, peak 3=ribonuclease A, peak 4=lysozyme, peak 5=α-amylase, and peak 6=insulin. It can be seen from comparing FIGS. 9 and 10 that the chromatographic cake and the chromatographic column produce generally comparable resolutions for the six proteins. But, the advantage of the chromatographic cake according to this invention is that the thickness of the chromatographic cake is only 1/40 the length of the chromatographic column with substantially the same geometric volumes of the respective packed beds. This Example thus shows that satisfactory chromatographic resolution is achieved with the chromatographic cakes of this invention even though they are configured with a relatively larger diameter and relatively short column length, but with the same geometric volume as a conventional chromatographic column.

EXAMPLE 7

Separations Using Different Types of Chromatographic Cakes

Figure 11:
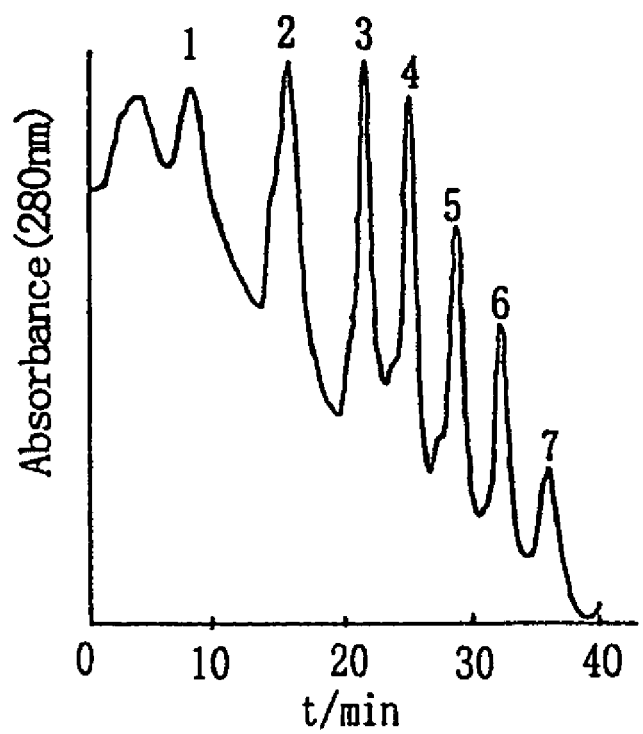
FIG. 11 is a chromatogram resulting from use of a 10×50 mm I.D. chromatographic cake in accordance with this invention to separate seven standard proteins.
Figure 12:
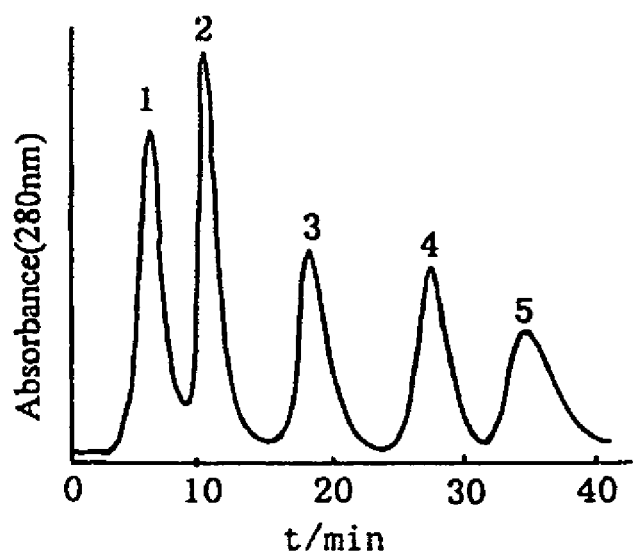
FIG. 12 is a chromatogram resulting from use of a 10×200 mm I.D. chromatographic cake in accordance with this invention to separate five standard proteins.
Figure 13:
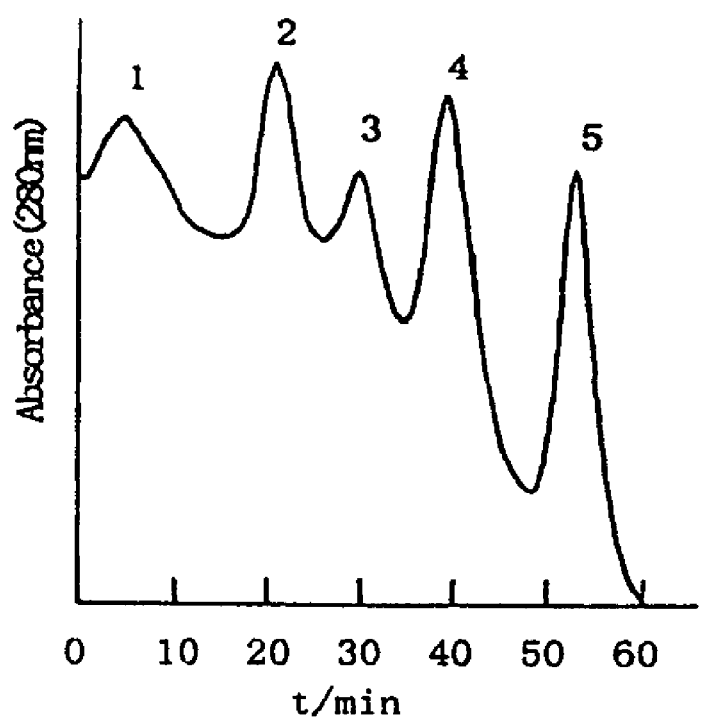
FIG. 13 is a chromatogram resulting from the use of a 10×300 mm I.D. chromatographic cake in accordance with this invention to separate five standard proteins.

In this Example, the standard proteins were separated using three sizes of chromatographic cakes manufactured in accordance with this invention, namely a 10×50 mm I.D. cake, a 10×200 mm I.D. cake and a 10×300 mm I.D. cake. The results are shown respectively in FIGS. 11, 12 and 13. As shown in FIG. 11 wherein peak 1=cytochrome C, peak 2=myoglobin, peak 3=ribonuclease A, peak 4=lysozyme, peak 5=α-chmotropsen, peak 6=α-amylase, and peak 7=insulin, the proteins are separated under the chromatographic conditions of 5.0 mL/min. flow rate, 0.08 AUFS, and a gradient ranging from 100% A to 100% B for a period of 40 mins. As shown in FIG. 12, wherein peak 1=cytochrome C, peak 2=myoglobin, peak 3=lysozyme, peak 4=α-amylase, and peak 5=insulin, the proteins are separated under the chromatographic conditions of 100.0 ml/min. flow rate, 0.05 AUFS, and a gradient ranging from 100% A to 100% B for a period of 40 mins. As shown in FIG. 13, wherein peak 1=cytochrome C, peak 2=myoglobin, peak 3=ribonuclease A, peak 4=lysozyme, and peak 5=α-amylase, the proteins are separated under the chromatographic conditions of 120.0 ml/min. flow rate, 0.1 AUFS, and a gradient ranging from 100% A to 100% B for a period of 60 mins. It can be seen in the Figures that all of these chromatographic cakes with different specifications result in satisfactory resolution.

EXAMPLE 8

Renaturation Efficiency of Denatured Lysozyme with Urea and Guanidinine Hydrochloride Using a Chromatographic Cake In this Example, under two different chromatographic conditions, sample injections were made of denatured lysozyme into solutions of urea and guanidinine hydrochloride (GuHCl), after the 5×50 mm I.D. chromatographic cakes in accordance with this invention were equilibrated with solution A. Then the renatured components coming from the chromatographic cakes were collected. The bioactivity recovery of these effluent streams was measured as shown in Table 1 below. The gradient used was changed from 100% A to 100% B. It can be seen from the results in Table 1 that the chromatographic cake has a substantial renaturation effect on the denatured lysozyme by urea and GuHCl.

TABLE 1

Bioactivity recovery of Lysozyme under different chromatographic conditions

| Sample | Flow rate, 4 mL/min. 25 min. linear gradient time | Flow rate, 2. mL/min. 50 min. linear gradient time |
| --- | --- | --- |
| Denatured Lysozyme by urea | 102.9% | 104.7% |
| Denatured Lysozyme by GuHCl | 103.7% | 104.0% |

EXAMPLE 9

Figure 14:
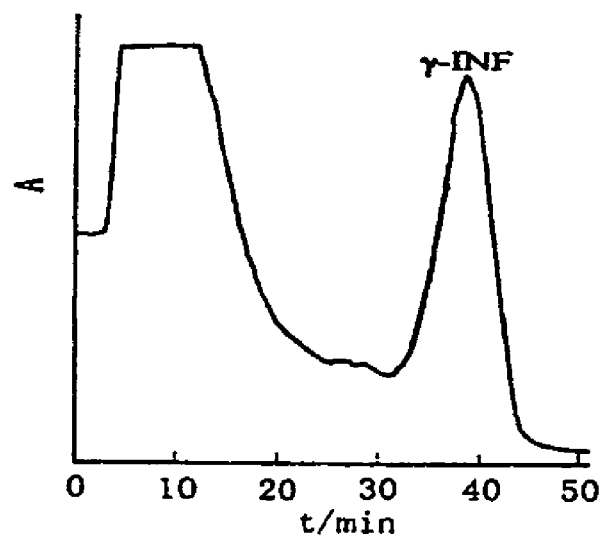
FIG. 14 is a chromatogram resulting from renaturation carried out with simultaneous purification of rhINF-γ using a 10×50 mm I.D. chromatographic cake in accordance with this invention.

Renaturation with Simultaneous Purification of the Recombined Human Interferon rhINF-γ Using a Chromatographic Cake FIG. 14 shows the chromatographic results of this Example in which renaturation is carried out simultaneously with purification of rhINF-γ in a 10×50 mm I.D. chromatographic cake in accordance with this invention. The sample used was an rhINF-γ solution extracted from the cellular cataclastic solution of *E. Coli* with 7.0 mol/L GuHCl solution. The bioactivity measuring method of rhINF-γ was the restraint method of cellular pathologic change. The operating conditions were as follows: the 7.0 mol/L GuHCl solution containing rhINF-γ of 1 mL was injected into the chromatographic cake equilibrated with mobile phase A from the extracting solution of *E. coli* at a flow rate of about 3.0–7.0 mL/min. over an interval of 25–40 mins., wherein the composition of the mobile phase was changed gradually from 100% A to 100% B. The fractions were collected and their bioactivities were measured separately. It can be seen in the results that the bioactivity recovery was 1774.57%, i.e., 17 times greater than the results achieved using the usual methods.

Industrial Applications

Figure 15:
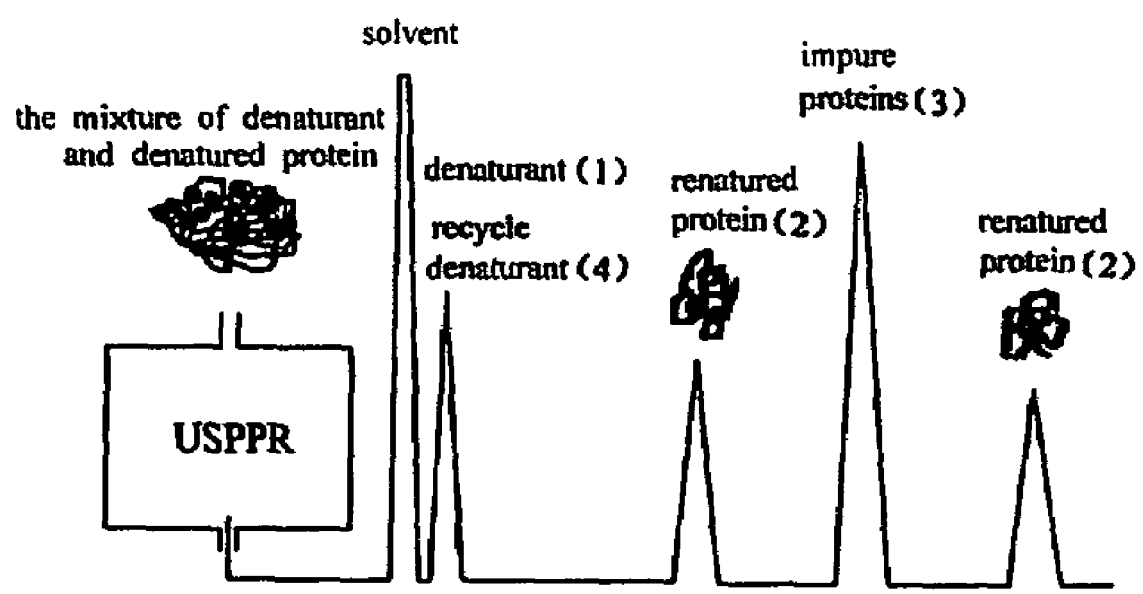
FIG. 15 schematically illustrates the multifunctional utility of chromatographic cakes in accordance with this invention.

Chromatographic cakes in accordance with this invention can be used successfully at a pressure of more than 20 Mpa. Such cakes do not deform during use, which helps to insure the surface evenness of the chromatographic packing at the end of a sample injection which, in turn, enhances the resolution. Using the cakes of this invention, separation is fast even with a low system pressure (e.g., lower than 5.0 Mpa generally). From the standpoint of good resolution under high flow rate conditions, the performance of chromatography cakes in accordance with this invention is comparable to that of perfusion chromatography and, therefore, has superior industrial applicability. The chromatographic cakes of this invention also allow for sample injections having a relatively high viscosity and a little precipitation. When the chromatographic separation is completed with the cakes of this invention, no fixed inlet and outlet are needed. The cakes of this invention show only a small irreversible absorption on objective products, which enhances the recovery of such objective products. With the chromatographic cake of this invention, the separation, renaturation, and purification processes can be performed in one step, which makes it at least three times simpler than the normal renaturation and purification technology. With the chromatographic cakes of this invention, the relevant production period can also be shortened by at least several times compared with comparable conventional processes and chromatographic devices. The investment for equipment is also reduced significantly using the chromatographic cakes of this invention. At the same time, denaturants can also be recovered when using chromatographic cakes in accordance with this invention. Not only can such recovered denaturants be reused, but also the environmental pollution caused by disposing of such denaturants can be reduced. FIG. 15 shows that a chromatographic cake in accordance with this invention can play a roll of "killing four birds with one stone", (that is, quick and complete elimination of denaturants, easy recycling of denaturants, protein renaturation, and separation of impure proteins). Using only the same packing volume as a conventional chromatographic column, in comparison with normal columns, more packing material can be packed into the inner cavity of a chromatographic cake packed in accordance with this invention. Relatively greater mass loading and volume loading is therefore possible with the chromatographic cakes of this invention.

Thus, the chromatographic cakes of this invention will find a wide range of applications in the separation, renaturation and purification of biopolymers.

While the present invention has been particularly shown and described above with reference to various exemplary embodiments thereof, it will be understood by those of ordinary skill in the art that various changes in form and details may be made therein without departing from the spirit and scope of the present invention, as defined by the following claims.

The invetion claimed is:

1. Chromatographic cake apparatus comprising in combination:
   a tubular body section open-ended at both ends defining a central axis and having at least a lateral opening therein, said lateral opening extending between an outer face of the body section and an inner face of the body section in a lateral direction that is generally orthogonal to the central axis;
   first and second clamp plates fastened respectively at first and second ends of the tubular body section so as to define a fixed volume inner cavity of said apparatus having a cavity thickness as measured along said central axis that ranges from about 0.2–50 mm and a lateral dimension of said cavity measured along said lateral direction that ranges from about 5.0–1000 mm, wherein the ratio of cavity thickness to lateral dimension does not exceed 0.20;
   each of said first and second clamp plates having inner and outer clamp plate sides and a mobile phase inlet or outlet aperture along said central axis extending between the inner and outer clamp plate sides, said inlet or outlet aperture being capable of passing a mobile phase through a central portion of said clamp plate respectively into or out of said inner cavity; and, first and second frit elements positioned on the inner clamp plate sides adjacent an end of said inner cavity, each frit element comprising frit holes of a frit hole size so as to retain particulate chromatographic material having an average particle size greater than the frit hole size inside the inner cavity, while permitting passage of a mobile phase containing a material sized to pass through the frit holes.

2. A chromatographic cake apparatus according to claim 1 further comprising first and second distributor elements, each positioned between a frit element and its associated clamp plate, said distributor elements comprising suitably sized plate members having on at least one face thereof multiple radiating grooves intersecting multiple concentric circular grooves wherein the junctions between the radiating grooves and the circular grooves are mobile phase distribution holes.

3. A chromatographic cake apparatus according to claim 2, further wherein the diameters of the mobile phase distribution holes gradually increase as they are located further radially outward from the center of the distributor element.

4. A chromatographic cake apparatus according to claim 1, further wherein the inner cavity is generally round in shape with a thickness of about 10 mm and having a diameter in the range of about 50 mm to 300 mm.

5. A chromatographic cake apparatus according to claim 1 further comprising first and second seal rings, each positioned between an end of the tubular body section and the associated clamp plate, effective to seal the inner cavity except at said mobile phase inlet and outlet apertures and at said lateral opening.

6. A chromatographic cake apparatus according to claim 1 wherein said body section, said clamp plates, and said frit elements are made of stainless steel to accommodate operational pressures in the range of 1–200 kg/cm$^2$.

7. A chromatographic cake apparatus according to claim 1 wherein the cavity thickness ranges from about 0.2 to 50 mm, the corresponding lateral dimension ranges from about 5.0 to 1000 mm, and the ratio of the cavity thickness to lateral dimension is about 0.20 to 0.033.

8. A chromatographic cake apparatus according to claim 1 wherein said tubular body section has a cross-sectional shape selected from round, polygonal, or elliptical.

9. A chromatographic cake apparatus according to claim 1 wherein said tubular body section has a cross-sectional shape selected from round, polygonal, or elliptical.

10. Chromatographic cake apparatus comprising in combination:

a tubular body section open-ended at both ends defining a central axis and having at least a lateral opening therein, said lateral opening extending between an outer face of the body section and an inner face of the body section in a lateral direction that is generally orthogonal to the central axis;

first and second clamp plates fastened respectively at first and second ends of the tubular body section so as to define a fixed volume inner cavity of said apparatus having a cavity thickness as measured along said central axis that ranges from about 0.2–50 mm and a lateral dimension of said cavity measured along said lateral direction that ranges from about 5.0–1000 mm, wherein the ratio of cavity thickness to lateral dimension does not exceed 0.20;

each of said first and second clamp plates having inner and outer clamp plate sides and a mobile phase inlet or outlet aperture along said central axis extending between the inner and outer clamp plate sides, said inlet or outlet aperture being capable of passing a mobile phase through a central portion of said clamp plate respectively into or out of said inner cavity;

first and second frit elements positioned on the inner clamp plate sides adjacent an end of said inner cavity, each frit element comprising frit holes of a frit hole size so as to retain particulate chromatographic material having an average particle size greater than the frit hole size inside the inner cavity, while permitting passage of a mobile phase containing a material sized to pass through the frit holes;

an end cap sealing said lateral opening; and, a chromatographic packing material having an average particle size that is larger than the frit hole size packed into said inner cavity.

11. A chromatographic cake apparatus according to claim 10 further comprising first and second distributor elements, each positioned between a frit element and its associated clamp plate, said distributor elements comprising suitably sized plate members having on at least one face thereof multiple radiating grooves intersecting multiple concentric circular grooves wherein the junctions between the radiating grooves and the circular grooves are mobile phase distribution holes.

12. A chromatographic cake apparatus according to claim 10, further wherein the diameters of the mobile phase distribution holes gradually increase as they are located further radially outward from the center of the distributor element.

13. A chromatographic cake apparatus according to claim 10, further wherein the inner cavity is generally round in shape with a thickness of about 10 mm and having a diameter in the range of about 50 mm to 300 mm.

14. A chromatographic cake apparatus according to claim 10 further comprising first and second seal rings, each positioned between an end of the tubular body section and the associated clamp plate, effective to seal the inner cavity except at said mobile phase inlet and outlet apertures and at said lateral opening.

15. A chromatographic cake apparatus according to claim 10 wherein said body section, said clamp plates, and said frit elements are made of stainless steel.

16. A chromatographic cake apparatus according to claim 10 wherein the cavity thickness ranges from about 0.2 to 50 mm, the corresponding lateral dimension ranges from about 5.0 to 1000 mm, and the ratio of the cavity thickness to lateral dimension is about 0.20 to 0.033.

17. Chromatographic cake apparatus comprising in combination:

a tubular body section open-ended at both ends defining a central axis and having at least a lateral opening therein, said lateral opening extending between an outer face of the body section and an inner face of the body section in a lateral direction that is generally orthogonal to the central axis;

first and second clamp plates fastened respectively at first and second ends of the tubular body section so as to define a fixed volume inner cavity of said apparatus having a cavity thickness as measured along said central axis that is about 0.20 to 0.033 time the lateral dimension of said cavity measured along said lateral direction;

each of said first and second clamp plates having inner and outer clamp plate sides and a mobile phase inlet or outlet aperture along said central axis extending between the inner and outer clamp plate sides, said inlet or outlet aperture being capable of passing a mobile phase through a central portion of said clamp plate respectively into or out of said inner cavity; and, first and second frit elements positioned on the inner clamp plate sides adjacent an end of and said inner cavity, each frit element comprising frit holes of a frit hole size so as to retain particulate chromatographic material having an average particle size greater than the frit hole size inside the inner cavity, while permitting passage of a mobile phase containing a material sized to pass through the frit holes.

* * * * *